US00PP28791P3

(12) United States Plant Patent
Mayo et al.

(10) Patent No.: US PP28,791 P3
(45) Date of Patent: Dec. 26, 2017

(54) APPLE TREE NAMED 'MAYO'

(50) Latin Name: *Malus domestica*
Varietal Denomination: Mayo

(71) Applicants: William L. Mayo, Franklin, VT (US); Susan B. Mayo, Franklin, VT (US)

(72) Inventors: William L. Mayo, Franklin, VT (US); Susan B. Mayo, Franklin, VT (US)

( * ) Notice: Subject to any disclaimer, the term of this patent is extended or adjusted under 35 U.S.C. 154(b) by 0 days.

(21) Appl. No.: 14/998,903

(22) Filed: Mar. 1, 2016

(65) Prior Publication Data

US 2017/0257992 P1 Sep. 7, 2017

(51) Int. Cl.
*A01H 5/08* (2006.01)

(52) U.S. Cl.
USPC ..... Plt./161

(58) Field of Classification Search
USPC ..... Plt./161
See application file for complete search history.

*Primary Examiner* — Annette H Para
(74) *Attorney, Agent, or Firm* — Polster Lieder Woodruff & Lucchesi, L.C.

(57) ABSTRACT

A new and distinct Apple Tree named 'Mayo' characterized particularly by a combination of great scab and cedar apple rust resistance, greater hardiness, its fruit having a white, crisp flesh, its sweetness in taste and goodness for eating, uniquely balanced with a dry bittersharp quality which makes it particularly suitable for blending purposes in the production of hard apple cider.

6 Drawing Sheets

CROSS-REFERENCE TO RELATED APPLICATIONS

Not Applicable.

STATEMENT REGARDING FEDERALLY SPONSORED RESEARCH

Not Applicable.

BACKGROUND

The present invention relates to a new and distinct variety of *Malus domestica,* an apple tree, discovered as a chance seedling, which we refer to as an Apple Tree named 'Mayo'. The apple tree is a deciduous tree of the rose family known for its pomaceous fruit. Applicant's new cultivar bears fruit annually.

Discovery

The inventors have been growing apple trees in Franklin, Vt. since 1996. In 2008, they, by chance, observed a seedling of unknown parentage from which they obtained buds used to reproduce their Apple Tree named 'Mayo'.

Propagation

Asexual reproduction by budding trees using buds obtained from the seedling discovered in 2008. The tree was asexually propagated on the site location and observed. Further reproduction using scion wood provided was asexually reproduced by Stark Bro's Nurseries & Orchards co. at their facilities in Louisiana, Mo.

Uniqueness

The new 'Mayo' cultivar differs from parents and related cultivars in that it is characterized by a combination of greater scab and cedar apple rust resistance, greater hardiness, a distinct white, crisp flesh, and increased sweetness, uniquely balanced with a dry bittersharp quality that makes it desirable for blending in the production of hard apple cider.

Use

The tree and its fruit were observed for a period of time and are believed to be particularly useful anywhere apple trees are raised; for example, in fruit tree orchards, field nurseries, or in a landscape setting, and more particularly in these settings throughout the United States. The fruit produced by the new cultivar is a superior cider apple classified as a "bittersharp" apple having a high sugar content and a low pH. Extensive testing and evaluation of the fruit has found its juice to be excellent when used for blending purposes in the production of hard cider, with the juice from the apple fruit valued for its superior astringency (dryness).

Industry Representation

*Malus domestica* and related varieties are disclosed in a number of plant patents. With respect to varieties in which the fruit may be used in making cider, these include: U.S. Plant Pat. No. 18,485 for a non-browning apple cultivar named 'SJCA38R6A74'; U.S. Plant Pat. No. 12,863 for a Mackintosh apple variety named Mariela; and U.S. Plant Pat. No. 7,209 for an apple tree: Keystone. Other representative apple trees include U.S. Plant Pat. No. 7,197 for an apple tree cultivar: 'Honeycrisp'.

BRIEF SUMMARY OF THE NEW VARIETY

The disclosed and claimed apple tree is a new distinct cultivar which annually produces fruit that is normally ripe for harvesting and shipping on or about October 5$^{th}$ under the ecological and climatological conditions prevailing around approximately 45° north latitude in the Franklin, Vt. area of New England. The fruit is most notable for its use as a blend for making hard cider as documented by cider producers, commercial nurseries, and lab testing.

The present variety produces a medium sized pome. The fruit is typically red and carmine over yellow in color when ripe. The flesh of the fruit is white when the fruit is ripe.

BRIEF DESCRIPTION OF THE PHOTOGRAPHS

The accompanying photographs depict the color of the tree and foliage of our new variety as nearly as is reasonably possible to make the same in a color illustration of this character.

DETAILED DESCRIPTION OF THE NEW VARIETY

The following is a detailed description of our new 'Mayo' cultivar with color terminology in accordance with The Royal Horticultural Society (R.H.S.) Colour Chart except where the context indicates a term having its ordinary dictionary meaning. Our new tree has not been observed under all growing conditions and variations may occur as a result of different growing conditions. All progeny of our new 'Mayo' cultivar, insofar as have been observed, have been identical in all the characteristics described below.

Other than as set forth below, as of this time, no other characteristics of our new Apple Tree have been observed by the inventors which are different from the characteristics common to apple trees.

Parentage: A true chance seedling first observed in 2008. Using buds from that mutation, additional trees were budded.

Locality where grown and observed: Franklin, Vt. It is believed that the apple tree observed for the detailed botanical description below is estimated to be at least sixty years old. The 'Mayo' cultivar was grown on Bud. 118 rootstock at the original site location for observation, in which the following observations were made.

Tree:

*Size.*—Average for the species.

*Vigor.*—Vigorous and hardy under typical climatic conditions around Franklin, Vt., which is approximately 45° north latitude. The tree has proven hardy in the field at the Franklin, Vt. location. It has no apparent winter injury and bears fruit annually. Meteorological data indicates a 60+ year old tree, which could be the parent tree, being exposed to temperatures of −34° F. with no measurable damage to tree tissue or budwood.

Figure 1:
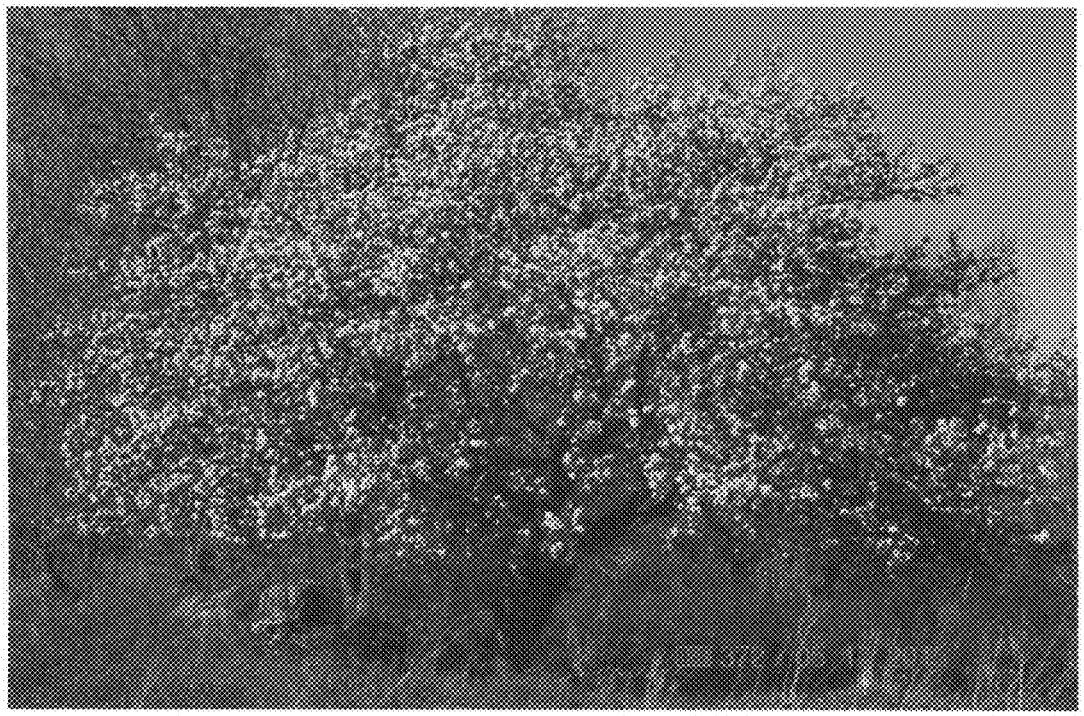
FIG. 1 is a photograph of a new and distinct variety of apple tree named the "Franklin Cider Apple" tree when the tree is in bloom.

*Tree form.*—Considered slightly upright to upright dense. See FIG. 1.

*Tree height.*—When measured at the end of the 2015 growing season, the present variety had a height to about 7.3 meters to about 7.9 meters. See FIG. 1.

*Tree crown.*—Width — Approximately 12 meters. See FIG. 1.

*Productivity.*—Very Productive.

*Regularity of bearing.*—Regular.

*Trunk diameter.*—When measured at a distance of approximately 20 centimeters above ground level the variety has a trunk diameter of approximately 33.02 centimeters.

Figure 3:
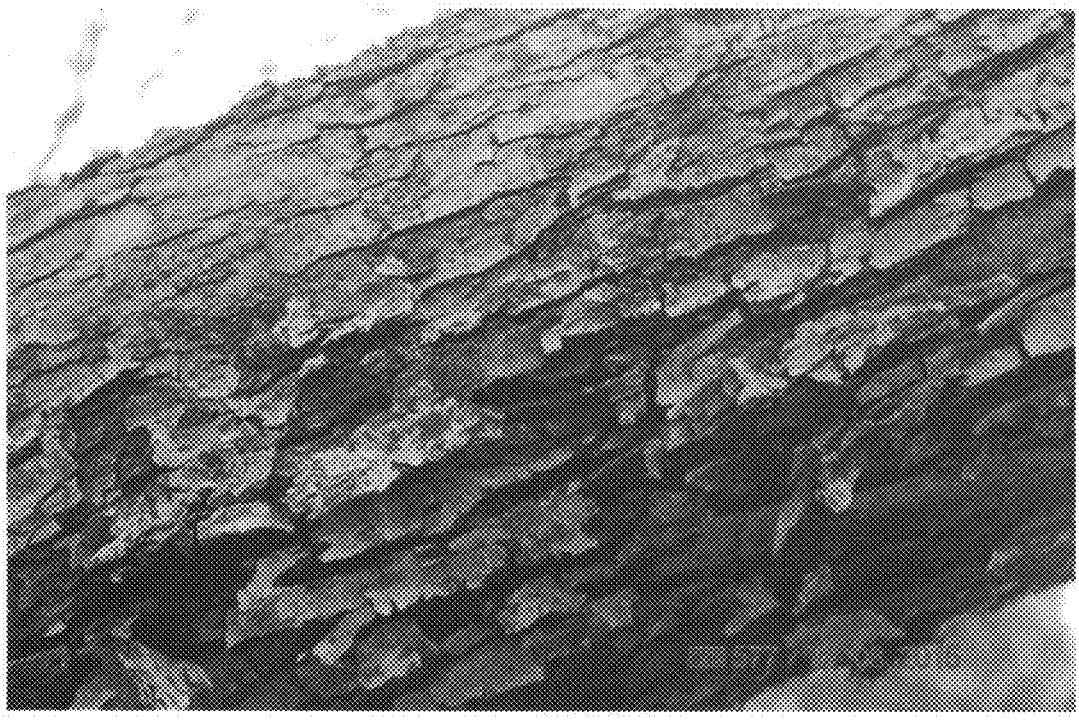
FIG. 3 is a photograph showing the bark of the tree.

Bark:

*Surface texture.*—Rough. See FIG. 3.

*Bark color.*—Considered reddish brown (RHS Fan 4, Sheet 200C).

*Bark lenticels.*—Numbers — Numerous and appearing roughened on their surfaces.

*Lenticels.*—Shape — Considered oval.

*Lenticels.*—Size — Approximately 1.5 to about 2.0 millimeters in width, and from about 1.0 to about 1.25 millimeters in height.

*Lenticels.*—Color — Orange (RHS Fan 4, Sheet 168B).

Figure 4:
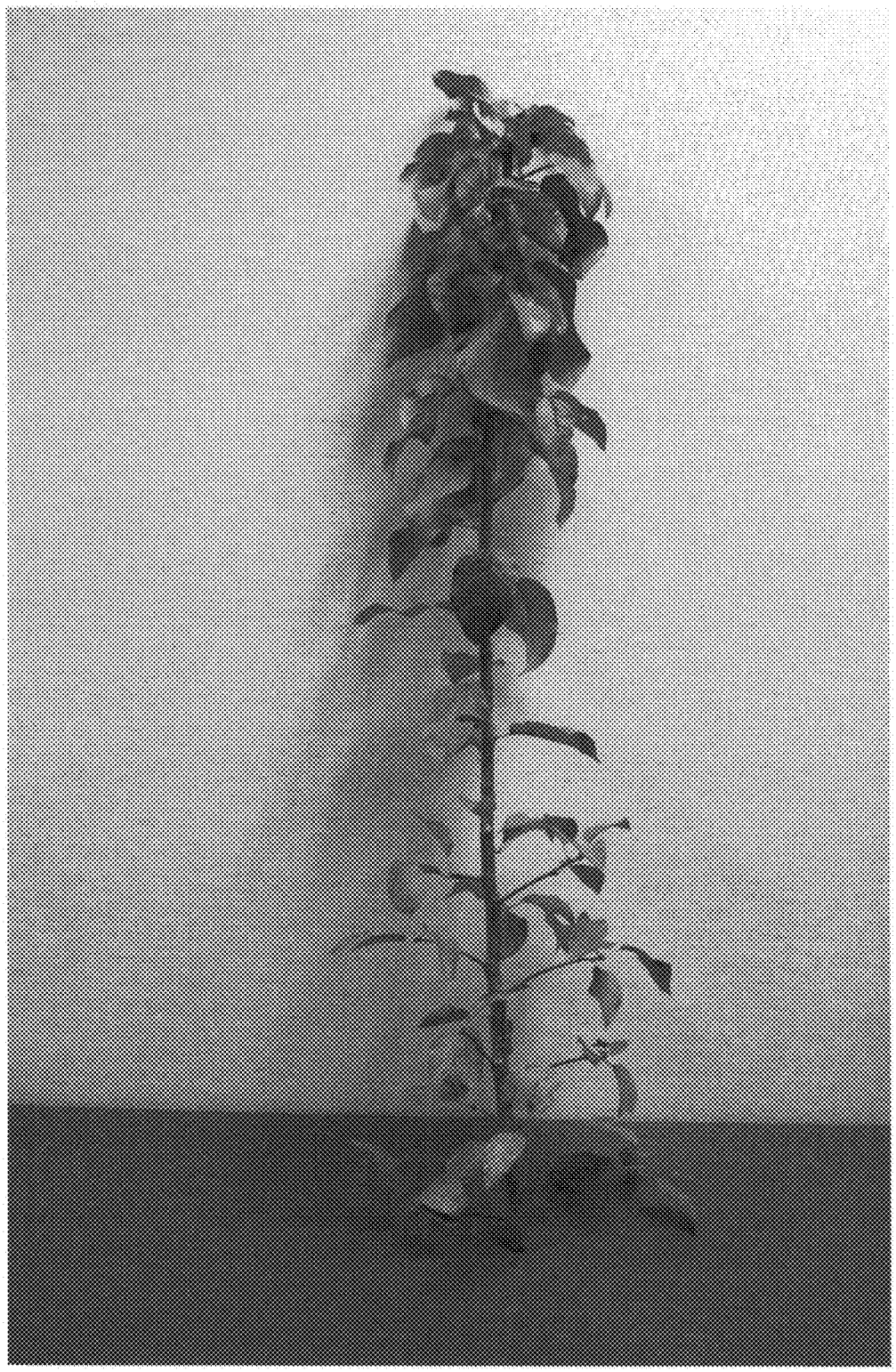
FIG. 4 is a photograph of a limb or branch of the tree showing its leaves.

Branches:

*Size.*—Considered normal in diameter for the species. The main scaffold branches of the observed tree range in diameter from about 15.00 centimeters to about 18.75 centimeters when measured at the base of the scaffold. See FIG. 4.

*Surface texture.*—Scaffold branches appear smoother than the trunk surface, but have approximately the same grey color (RHS Fan 4, Sheet 202C). See FIG. 4.

*Lenticels.*—The lenticels seen on the branches appear to be much less pronounced or evident as that of the trunk, noted above.

*Upper branches.*—Size — The upper spreader branches range in size from about 4.60 to about 6.40 centimeters in diameter at their bases, while smaller hanger branches vary in thickness from about 0.79 to about 1.27 centimeters.

*Surface texture.*—Older branches — Two year old or older branches appear to have the same surface texture, and further have numerous medium brown colored and calloused lenticels (RHS Fan 4, Sheet 164C).

*Older branches.*—Color — Reddish brown in color and nearly glabrous in surface texture (RHS Fan 4, Sheet 200B).

*One year old shoots and spurs.*—Color — Considered reddish brown in color (RHS Fan 4, Sheet 200C) and having a moderately pubescent surface texture.

*Current season's shoots.*—Color — Greyed-Orange (RHS Fan 4, Sheet 1778). These current season's shoots have a moderately pubescent surface texture. Cultivar is a profuse producer of spiny limbs.

Figure 2A:
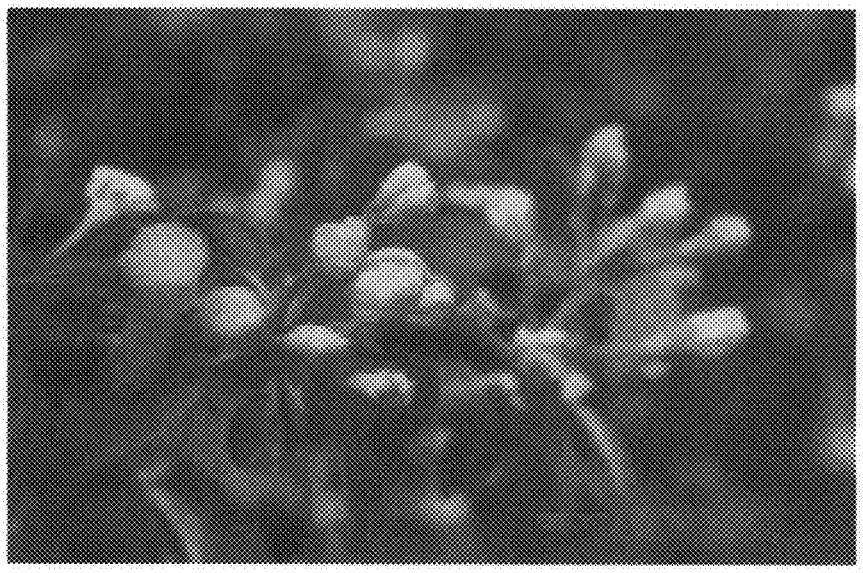
FIG. 2A is a photograph showing buds of the tree and FIG. 2B is a photograph of the blooms of the tree.
Figure 2B:
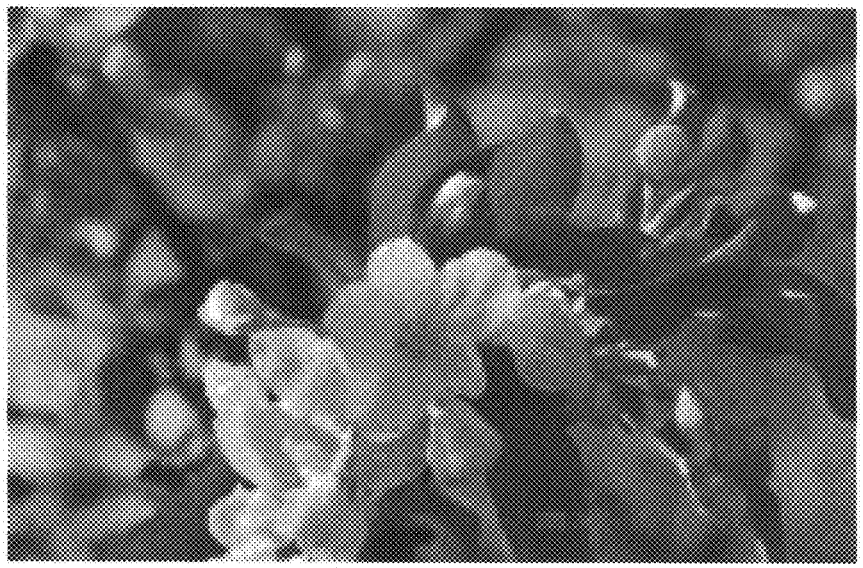

*Actively growing shoots.*—Color — Green-brown (RHS Fan 4, Sheet 177C). Actively growing shoots have a highly pubescent surface texture of medium length. The pubescence appears wooly. Very vigorous growth. See FIG. 2.

*Expanding shoot tips and young leaves.*—Color — Considered green in coloration (RHS Fan 3, Sheet 134C).

*Internode length.*—When measured on upright vigorous shoots, this ranges from about 2.5 to 3.0 centimeters between adjacent nodes. The length between the nodes as seen on smaller lateral shoots ranges from about 1.5 to about 2.0 centimeters.

Figure 5:
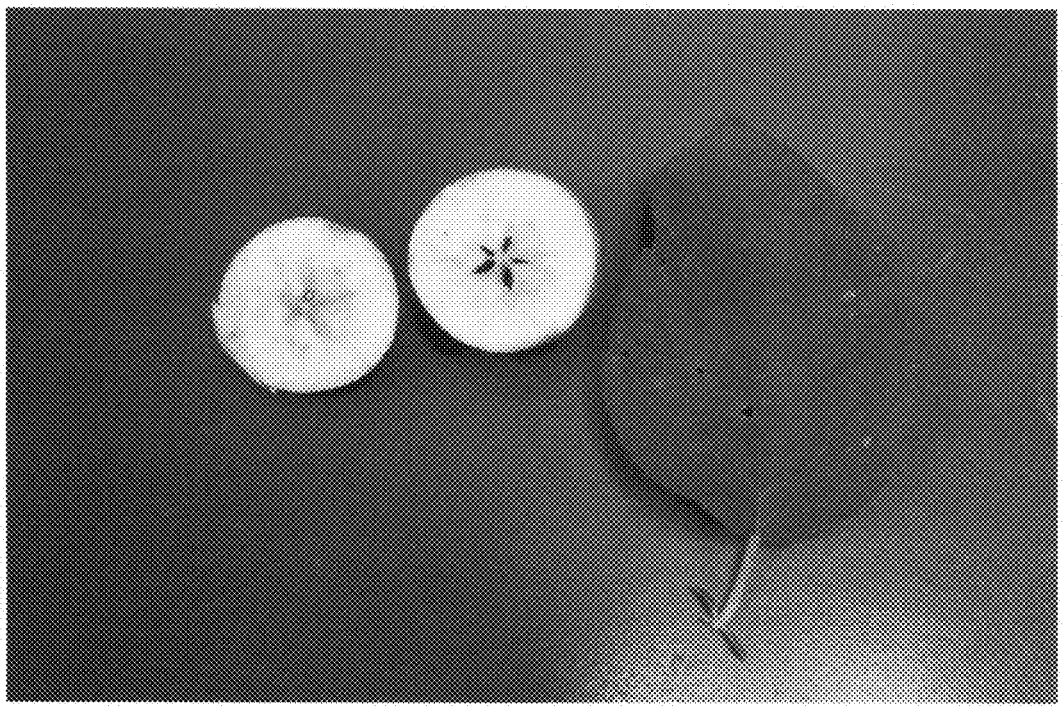
FIG. 5 is a photograph showing a leaf of the tree.

Leaves:

*Size.*—Generally — Considered medium to large for the species. The measurements which follow have been taken from leaves growing near mid-shoot on vigorously growing current season's shoots. See FIG. 5.

*Leaf length.*—About 13.0 to about 13.5 centimeters including the leaf petiole. See FIG. 5.

*Leaf width.*—About 6.0 to about 6.5 centimeters. See FIG. 5.

*Leaf thickness.*—Considered normal for the species.

*Surface texture.*—Young immature leaves are highly pubescent on both the upper and lower leaf surfaces. As these leaves mature, however, much of this pubescence is lost.

*Mature leaf texture.*—Very slightly rugose. No glands are evident on the leaf.

*Leaf form.*—Generally — Considered variable from broadly lanceolate to ovate.

*Leaf apices.*—Shape — Acute and at times curled backward from the upper leaf surface. Most leaves appear somewhat folded upwards.

*Leaf surface.*—Texture — The leaf surfaces along the mid-vein are, at some locations, slightly wavy.

*Leaf color.*—Mature leaves — The upper leaf surface appears dark green (RHS Fan 3, Sheet 137A); and the lower surfaces are a lighter green in color (RHS Fan 3, Sheet 138B).

*Color.*—Mid-Vein — The primary mid-vein on the lower leaf surface is a pale yellow-green (RHS Fan 3, Sheet 145C).

*Leaf margins.*—Generally — Considered serrate and tipped with narrow, soft, sharp spines.

*Serrations.*—Size — Moderately small.

*Leaf margins.*—Shape — Slightly undulate.

*Leaf petiole.*—Size — Considered average and short, and further having a length of about 2.5 to about 3.0 centimeters, and a thickness of about 2.0 to 2.5 millimeters when measured at approximately mid-petiole.

*Petiole base.*—Shape — Typically considered wider and at times slightly flared, and having a thickness of about 3.0 to about 3.5 millimeters.

*Petiole.*—Color — Considered yellow-green on younger leaves (RHS Fan 3, Sheet 144D) and on older leaves (RHS Fan 3, Sheet 145C). Within the petiole groove and the petiole ridges, the color is increasingly darker (RHS Fan 3, Sheet 138B).

*Petiole.*—Surface texture — Lightly pubescent.

*Immature leaves.*—Surface texture — The leaves appear to have a higher degree of pubescence than mature leaves. No glands are present on the petiole.

*Leaf stipules.*—Generally — About 1.5 to about 2.0 millimeters in length and about 2.0 to about 3.0 millimeters in width.

*Leaf stipules.*—Form — Considered linearly lanceolate. The leaf stipules darken and deteriorate within increasing senescence.

Flowers:

*Flower buds.*—Size — Generally considered large, plump and conic in form. The buds are considered relatively free from the bearing stem and are considered hardy under Franklin, Vt. climatic conditions. See FIG. 2.

*Flower buds.*—Color — Reddish pink (RHS Fan 1, Sheet 50C) to white.

*Flower buds.*—Surface texture — Considered pubescent especially apically and over the interior side of the bud scales.

*Bloom time.*—Generally — Average to slightly early in relative comparison to other common cider apple tree varieties growing at the same geographic location. See FIG. 2B.

*Date of full bloom.*—Observed at Franklin Vt. on May 12, 2014 and May 14, 2015.

*Duration of bloom.*—The date and duration of bloom can be substantially effected by the amount of chilling hours that occur during a given year, and the geographical location where the variety is grown.

*Flower size.*—Generally — about 31.00 to about 33.00 millimeters wide.

*Bloom quantity.*—Considered abundant.

*Flowers per node.*—As many as five can be produced.

*Petal numbers.*—Typically five, but extra petals can be observed. As many as 5 extra petals can sometimes be seen.

*Petal form.*—Considered variable, but most frequently appears ovate.

*Petal color.*—White (RHS Fan 4, Sheet 155D) with some pink shading (RHS Fan 4, Sheet N155C) around the margins.

*Petal claw.*—Shape — Ovate.

*Petal margins.*—Shape — Undulate.

*Petal apices.*—Form — Variable and having a somewhat pointed tip.

*Flower pedicel.*—Size — These are variable from about 25.00 to about 30.00 millimeters in length, and from about 26.00 to about 31.00 millimeters in thickness.

*Flower pedicel.*—Color — Pale green (RHS Fan 3, Sheet 145C).

*Flower pedicel.*—Surface Texture — Pubescent, and further having moderately sparse filamentous pubescence.

*Floral nectaries.*—Color — Yellow-brown (RHS Fan 3, Sheet 153B). The floral nectaries become darker with increasing senescence.

*Calyx.*—Surface Texture — Slightly pubescent.

*Calyx.*—Color — Pale green (RHS Fan 3, Sheet 1456).

*Sepals.*—Surface Texture — Pubescent.

*Sepals.*—Size — Relatively small and elongated in form.

*Sepals.*—Color — Green-yellow (RHS Fan 3, Sheet 151B).

*Anthers.*—Size — Considered average for the species.

*Anthers.*—Color — Considered a light yellow (RHS Fan 1, Sheet 2C). This color appears both ventrally and dorsally.

*Pollen production.*—Considered abundant in quantity.

*Pollen.*—Color — Yellow (RHS Fan 1, Sheet 2C).

*Stamens.*—Color — White (RHS Fan 4, Sheet 155D) to pink (RHS Fan 1, Sheet 50D); about 4 to about 6 millimeters in length.

*Pistil.*—Form — The pistil of the present variety has five styles separated to the ovary.

*Pistil.*—Length — Somewhat variable from about 6 to 7 millimeters.

*Pistil.*—Surface Texture — Glabrous.

*Pistil.*—Color — Yellow-green (RHS Fan 1, Sheet 1D).

Fruit:

*Maturity when described.*—The fruit of the present variety of our new 'Mayo' Apple tree is described at full commercial maturity hereinafter.

*Date of harvest.*—In 2013, the date of harvest was October 25. The date of harvest in 2014 was October 29. The date of harvesting, noted above, are those that were observed at Franklin, Vt. In addition, the fruit exhibits sufficient hardiness that the harvest season could be extended for a longer period than that of most current varieties.

Figure 6:
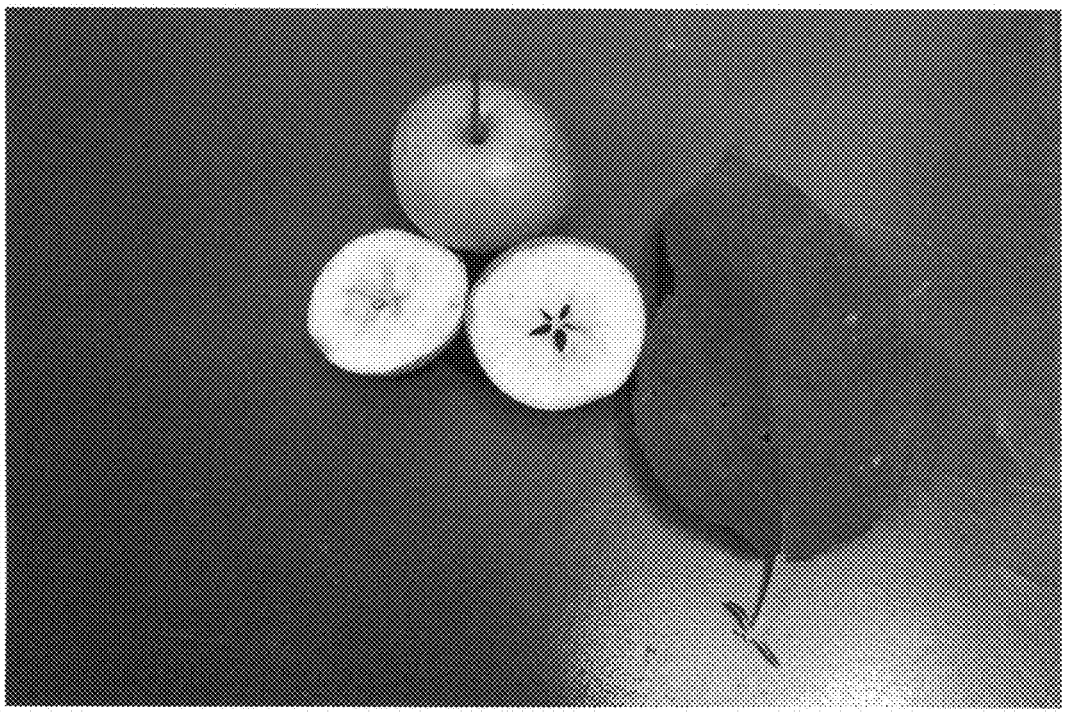
FIG. 6 is a photograph showing the fruit of the tree, both whole and sliced.

*Fruit size.*—Generally — The fruit diameter was about 4.5 to about 5.0 centimeters adjacent the stem and about 3.5 to about 4.0 centimeters around the base; the fruit had a height of about 4.0 to about 4.5 centimeters. See FIGS. 5 and 6.

*Fruit form.*—Generally — conical. See FIGS. 5 and 6.

*Fruit symmetry.*—Somewhat variable, from fully symmetrical to slightly asymmetrical. See FIG. 6.

*Fruit stem.*—Size — The fruit stem has a length dimension of about 10.0 to about 15.0 millimeters; and a thickness dimension of about 1.0 to about 1.5 millimeters. See FIG. 6.

*Fruit stem.*—Shape — Typically, considered slightly curved. See FIG. 5.

*Fruit stem.*—Color — Light green (RHS Fan 3, Sheet 144B). See FIG. 6.

*Fruit stem.*—Surface Texture — Moderately pubescent. See FIG. 6.

*Fruit lenticels.*—Color — Light tan and being slightly raised and oval in form on the fruit stem surface (RHS Fan 4, Sheet 161A).

*Stem cavity.*—Shape — Considered uniform and acute.

*Stem cavity.*—Size — Considered moderate. The width of the stem cavity ranges from about 13.0 to about 15.0 millimeters when measured across the shoulders of the fruit. The depth of the stem cavity is variable from about 4.0 to about 6.0 millimeters.

*Fruit basin.*—Shape — Symmetrical, approximately 4.0 millimeters in depth and approximately 15.0 millimeters in breadth.

*Calyx.*—Form — The calyx opening is closed.

*Core.*—Medium. Bundle area — medium small; oblate symmetrical; acute at base. Bundle color — light green; inconspicuous, in one whorl. Core lines — clasping; in cross-section indistinct. Carpellary area — indistinct; small. Calyx tube — glabrous toward base; funnel-form. Stem of funnel — long. Depth of tube to shoulder — approximately 2.0 millimeter. Entire depth — approximately 4.0 millimeter. Styles — present; united toward base; pubescent toward base. Stamens — one distinct whorl; median. Seed cells — axile; closed. Cell walls — approximate; thin; tough. Length — approximately 6.0 millimeter. Breadth — approximately millimeter Longitudinal section — broadly ovate. Surface — smooth. Cross-section — narrow. See FIG. 5.

*Fruit carpels.*—Generally — Five carpels are present and are located within the fruit core. See FIG. 5.

*Fruit carpels.*—Shape — Star-shaped. See FIG. 5.

*Fruit carpel cells.*—Form — Generally speaking, these are closed in form although at times some open cells can be present.

*Fruit carpels.*—Surface Texture — The inner surface of the carpel wall is considered glabrous.

*Seeds.*—Numbers — Variable from 5 to as many as 8. See FIG. 5.

*Seeds.*—Size — Considered plump, and having a length of about 5.0 to about 7.0 millimeters; and a width from about 3.0 to about 4.0 millimeters.

*Seeds.*—Thickness — About 2.0 millimeters.

*Seed apex.*—Form — Acute.

*Seeds.*—Color — Dark Brown at full maturity (RHS Fan 4, Sheet 200D). The seeds color at full commercial maturity is also dark brown (RHS Fan 4, Sheet 200D).

*Fruit skin.*—Thickness — Considered average.

*Fruit skin.*—Surface texture — Smooth.

*Fruit skin.*—Flavor — Considered mild to neutral.

*Fruit skin.*—Color — Predominately red and carmine over yellow (RHS Fan 4, Sheet 179A) with variably placed russeting (RHS Fan 4, Sheet 163A) at full commercial maturity. See FIG. 5.

*Fruit skin.*—Lenticels — Few. These are small and relatively inconspicuous.

*Fruit skin lenticel color.*—Very pale yellow (RHS Fan 1, Sheet 1D). See FIG. 5.

*Bloom.*—None.

*Fruit flesh.*—Color — White with a very slight cream-yellow tint (RHS Fan 1, Sheet 11D). See FIGS. 5 and 6.

*Fruit flesh.*—Texture — Crisp and considered very juicy. See FIG. 5.

*Stone cells.*—Generally — Present, and average in number. The stone cells are located in the vicinity of the core area.

*Ripening.*—Considered even. The fruit holds well on the tree.

*Fruit flavor.*—Considered sweet, refreshing and mild, and having a very good commercial quality, particularly cider production. The fruit has a sugar content ranging from a low of 17.5 Brix (Specific Gravity 1.0785) to a high of 19.5 Brix (Specific Gravity 1.0808), giving it a finished potential alcohol content ranging from 9.8% to 11.1%.

*Aroma.*—Considered pleasant and slight.

*Resistance to insects and diseases.*—No particular susceptibility where noted. The present variety has not been intentionally tested to expose or detect any susceptibilities or resistance to any known plant and/or other fruit tree diseases. In addition, the fruit exhibits a scab resistance which alleviates the need to use certain types of chemical sprays on the tree thereby minimizing exposure risks to individuals and the environment while simultaneously lowering production costs.

What is claimed is:

1. A new and distinct apple tree named substantially as described and illustrated herein.

* * * * *